(12) United States Patent
Bain et al.

(10) Patent No.: US 8,562,629 B2
(45) Date of Patent: Oct. 22, 2013

(54) SUTURE DEVICE HAVING SELECTIVE NEEDLE ACTUATION AND RELATED METHOD

(75) Inventors: Gregory Bain, Irvine, CA (US); Kevin Baird, Phoenix, AZ (US); Vincent Tangherlini, Rancho Santa Margarita, CA (US); Norman Gordon, Irvine, CA (US)

(73) Assignee: ArthroCare Corporation, Austin, TX (US)

( * ) Notice: Subject to any disclaimer, the term of this patent is extended or adjusted under 35 U.S.C. 154(b) by 950 days.

(21) Appl. No.: 11/586,324

(22) Filed: Oct. 24, 2006

(65) Prior Publication Data

US 2008/0097482 A1    Apr. 24, 2008

(51) Int. Cl.
*A61B 17/04* (2006.01)

(52) U.S. Cl.
USPC ........................................................ 606/144

(58) Field of Classification Search
USPC .......................................... 606/144, 139, 148
See application file for complete search history.

(56) References Cited

U.S. PATENT DOCUMENTS

| | | | |
|---|---|---|---|
| 1,635,066 A | 7/1927 | Wells | 606/145 |
| 2,269,963 A | 1/1942 | Wappler | 604/61 |
| 2,286,578 A | 6/1942 | Sauter | 606/148 |
| 2,327,353 A | 8/1943 | Karle | 606/146 |
| 2,737,954 A | 3/1956 | Knapp | 606/146 |
| 2,738,790 A | 3/1956 | Todt, Sr. et al. | 606/145 |
| 3,842,840 A | 10/1974 | Schweizer | 128/334 |
| 3,946,740 A | 3/1976 | Bassett | |
| 4,027,608 A | 6/1977 | Arbuckle | 112/169 |
| 4,109,658 A | 8/1978 | Hughes | 128/340 |
| 4,164,225 A | 8/1979 | Johnson | 128/334 |
| 4,235,177 A | 11/1980 | Arbuckle | 112/169 |
| 4,345,601 A | 8/1982 | Fukuda | 128/339 |
| 4,373,530 A | 2/1983 | Kilejian | 128/334 R |
| 4,484,580 A | 11/1984 | Nomoto et al. | 606/146 |
| 4,493,323 A | 1/1985 | Albright et al. | 128/340 |
| 4,621,640 A | 11/1986 | Mulhollan et al. | |
| 4,635,637 A | 1/1987 | Schreiber | 128/337 |
| 4,738,255 A | 4/1988 | Goble et al. | 128/92 YF |
| 4,741,330 A | 5/1988 | Hayhurst | 128/43 R |
| 4,781,182 A | 11/1988 | Purnell et al. | 128/92 |
| 4,836,205 A | 6/1989 | Barrett | |
| 4,923,461 A | 5/1990 | Caspari | 606/146 |

(Continued)

FOREIGN PATENT DOCUMENTS

| | | |
|---|---|---|
| CA | 2205176 | 12/2000 |
| DE | 4235602 A1 | 4/1994 |

(Continued)

OTHER PUBLICATIONS

PCT International Search Report for PCT/US01/42186 3pgs, Mailed Feb. 13, 2002.

(Continued)

*Primary Examiner* — Corrine M McDermott
*Assistant Examiner* — Christina Lauer
(74) *Attorney, Agent, or Firm* — Matthew Scheele; Brian E. Szymczak

(57) ABSTRACT

Suturing instruments and methods for placing mattress stitches in soft tissue allowing the practitioner to selectively control placement of each stitch of the mattress stitch and/or place the stitch deeper into tissue by pulling tissue farther into the device are described herein.

17 Claims, 18 Drawing Sheets

(56) References Cited

U.S. PATENT DOCUMENTS

| | | | |
|---|---|---|---|
| 4,926,860 A | 5/1990 | Stice et al. ............... 606/146 |
| 4,935,027 A | 6/1990 | Yoon |
| 4,957,498 A | 9/1990 | Caspari et al. |
| 4,981,149 A | 1/1991 | Yoon et al. ............... 128/898 |
| 5,037,422 A | 8/1991 | Hayhurst et al. ........... 606/72 |
| 5,037,433 A | 8/1991 | Wilk et al. ............... 606/139 |
| 5,046,513 A | 9/1991 | Gatturna et al. ........... 128/898 |
| 5,059,201 A | 10/1991 | Asnis ............... 606/144 |
| 5,085,661 A | 2/1992 | Moss ............... 606/139 |
| 5,152,769 A | 10/1992 | Baber ............... 606/145 |
| 5,217,471 A | 6/1993 | Burkhart ............... 606/148 |
| 5,222,977 A | 6/1993 | Esser ............... 606/223 |
| 5,269,786 A | 12/1993 | Morgan ............... 606/96 |
| 5,304,184 A | 4/1994 | Hathaway et al. ........... 606/144 |
| 5,312,422 A | 5/1994 | Trott |
| 5,318,577 A | 6/1994 | Li ............... 606/147 |
| 5,336,229 A | 8/1994 | Noda |
| 5,356,424 A | 10/1994 | Buzerak et al. ............... 606/223 |
| 5,397,325 A | 3/1995 | Della Badia et al. |
| 5,403,329 A | 4/1995 | Hinchcliffe |
| 5,409,494 A | 4/1995 | Morgan ............... 606/96 |
| 5,417,699 A | 5/1995 | Klein et al. ............... 606/139 |
| 5,431,666 A * | 7/1995 | Sauer et al. ............... 606/139 |
| 5,445,167 A | 8/1995 | Yoon et al. ............... 128/898 |
| 5,454,823 A | 10/1995 | Richardson et al. .......... 606/148 |
| 5,474,565 A | 12/1995 | Trott |
| 5,480,405 A | 1/1996 | Yoon ............... 606/139 |
| 5,499,991 A | 3/1996 | Garman et al. |
| 5,501,688 A | 3/1996 | Whiteside et al. ........... 606/103 |
| 5,522,820 A | 6/1996 | Caspari et al. ............... 606/148 |
| 5,527,322 A | 6/1996 | Klein et al. ............... 606/144 |
| 5,540,705 A | 7/1996 | Meade et al. ............... 606/145 |
| 5,573,542 A | 11/1996 | Stevens ............... 606/144 |
| 5,575,801 A | 11/1996 | Habermeyer et al. ........ 606/144 |
| 5,609,597 A | 3/1997 | Lehrer ............... 606/139 |
| 5,613,974 A | 3/1997 | Andreas et al. ............... 606/144 |
| 5,618,290 A | 4/1997 | Toy et al. ............... 606/139 |
| 5,626,590 A | 5/1997 | Wilk ............... 606/148 |
| 5,645,552 A | 7/1997 | Sherts ............... 606/145 |
| 5,653,717 A | 8/1997 | Ko et al. ............... 606/144 |
| 5,665,108 A | 9/1997 | Galindo ............... 606/215 |
| 5,690,653 A | 11/1997 | Richardson et al. .......... 606/148 |
| 5,700,273 A | 12/1997 | Buelna et al. ............... 606/148 |
| 5,741,281 A | 4/1998 | Martin ............... 606/148 |
| 5,776,150 A | 7/1998 | Nolan et al. ............... 606/148 |
| 5,779,719 A | 7/1998 | Klein et al. ............... 606/144 |
| 5,792,151 A | 8/1998 | Heck et al. ............... 606/144 |
| 5,792,153 A | 8/1998 | Swain et al. ............... 606/144 |
| 5,797,927 A | 8/1998 | Yoon |
| 5,836,956 A | 11/1998 | Buelna et al. ............... 606/148 |
| 5,860,991 A | 1/1999 | Klein et al. ............... 606/145 |
| 5,860,992 A | 1/1999 | Daniel et al. |
| 5,902,311 A | 5/1999 | Andreas et al. ............... 606/144 |
| 5,904,692 A | 5/1999 | Steckel et al. ............... 606/139 |
| 5,908,426 A | 6/1999 | Pierce ............... 606/139 |
| 5,921,994 A | 7/1999 | Andreas et al. ............... 606/144 |
| 5,947,982 A | 9/1999 | Duran ............... 606/139 |
| 5,954,733 A | 9/1999 | Yoon ............... 606/147 |
| 5,957,937 A | 9/1999 | Yoon ............... 606/147 |
| 5,980,538 A | 11/1999 | Fuchs et al. ............... 606/145 |
| 5,984,933 A | 11/1999 | Yoon ............... 606/148 |
| 6,001,109 A | 12/1999 | Kontos ............... 606/148 |
| 6,022,360 A | 2/2000 | Reimels et al. ............... 606/144 |
| 6,024,747 A | 2/2000 | Kontos ............... 606/144 |
| 6,036,699 A | 3/2000 | Andreas et al. ............... 606/139 |
| 6,048,351 A | 4/2000 | Gordon et al. ............... 606/144 |
| 6,051,006 A * | 4/2000 | Shluzas et al. ............... 606/144 |
| 6,059,801 A | 5/2000 | Samimi ............... 606/148 |
| 6,096,051 A | 8/2000 | Kortenbach et al. .......... 606/144 |
| 6,117,144 A | 9/2000 | Nobles et al. |
| 6,136,010 A | 10/2000 | Modesitt et al. ............... 606/144 |
| 6,143,004 A | 11/2000 | Davis et al. ............... 606/144 |
| 6,143,005 A | 11/2000 | Yoon et al. ............... 606/148 |
| 6,214,028 B1 | 4/2001 | Yoon et al. ............... 606/205 |
| 6,217,592 B1 | 4/2001 | Freda et al. ............... 606/145 |
| 6,245,079 B1 | 6/2001 | Nobles et al. ............... 606/144 |
| 6,332,889 B1 | 12/2001 | Sancoff et al. ............... 606/148 |
| 6,533,795 B1 | 3/2003 | Tran et al. |
| 6,551,330 B1 | 4/2003 | Bain et al. |
| 6,605,096 B1 | 8/2003 | Ritchart ............... 606/144 |
| 6,770,084 B1 * | 8/2004 | Bain et al. ............... 606/144 |
| 6,893,448 B2 | 5/2005 | O'Quinn et al. ............... 606/139 |
| 6,896,686 B2 | 5/2005 | Weber ............... 606/145 |
| 6,911,034 B2 | 6/2005 | Nobles et al. ............... 606/144 |
| 6,923,819 B2 | 8/2005 | Meade et al. ............... 606/144 |
| 6,984,237 B2 | 1/2006 | Hatch et al. ............... 606/139 |
| 7,004,951 B2 | 2/2006 | Gibbens, III ............... 606/144 |
| 7,090,686 B2 | 8/2006 | Nobles et al. |
| 7,112,208 B2 | 9/2006 | Morris et al. ............... 606/144 |
| 7,160,309 B2 | 1/2007 | Voss ............... 606/144 |
| 7,169,157 B2 | 1/2007 | Kayan ............... 606/148 |
| 7,198,631 B2 | 4/2007 | Kanner et al. ............... 606/139 |
| 7,377,926 B2 | 5/2008 | Topper et al. ............... 606/144 |
| 7,449,024 B2 | 11/2008 | Stafford ............... 606/144 |
| 919,138 A1 | 4/2009 | Drake et al. |
| 7,585,305 B2 | 9/2009 | Dreyfuss ............... 606/144 |
| 7,666,195 B2 | 2/2010 | Kelleher et al. ............... 606/144 |
| 7,758,597 B1 | 7/2010 | Tran et al. ............... 606/144 |
| 7,879,048 B2 | 2/2011 | Bain et al. ............... 606/144 |
| 8,147,505 B2 | 4/2012 | Delli-Santi ............... 606/144 |
| 2002/0147456 A1 | 10/2002 | Diduch et al. ............... 606/144 |
| 2003/0065337 A1 | 4/2003 | Topper et al. ............... 606/144 |
| 2003/0181925 A1 | 9/2003 | Bain et al. ............... 606/144 |
| 2003/0195528 A1 | 10/2003 | Ritchart ............... 606/144 |
| 2003/0233106 A1 | 12/2003 | Dreyfuss ............... 606/144 |
| 2004/0010273 A1 | 1/2004 | Diduch et al. ............... 606/144 |
| 2004/0236353 A1 | 11/2004 | Bain et al. ............... 606/139 |
| 2004/0249394 A1 | 12/2004 | Morris et al. ............... 606/144 |
| 2005/0165419 A1 | 7/2005 | Sauer et al. ............... 606/148 |
| 2010/0241144 A1 | 9/2010 | Delli-Santi ............... 606/150 |
| 2011/0118760 A1 | 5/2011 | Gregoire et al. ............... 606/145 |

FOREIGN PATENT DOCUMENTS

| | | |
|---|---|---|
| DE | 2532242 A1 | 7/1995 |
| EP | 0535906 A2 | 4/1993 |
| EP | 1408849 B1 | 12/2010 |
| WO | 91/06247 | 5/1991 |
| WO | 97/10756 | 3/1997 |
| WO | 03/028532 | 4/2003 |
| WO | 2010/111176 | 9/2010 |

OTHER PUBLICATIONS

PCT International Preliminary Examination Report for PCT/US01/42186 3pgs, Sep. 9, 2003.
PCT International Search Report for PCT/US02/228869 2pgs, Mailed May 8, 2003.
PCT International Preliminary Examination Report for PCT/US02/22889 3pgs, Jan. 15, 2003.
PCT International Search Report for PCT/US03/18540 1pg, Mailed Oct. 15, 2003.
PCT International Preliminary Examination Report for PCT/US03/18540 4pgs, Aug. 24, 2004.
UK Search Report for GB 1019353.0, 4pgs, Mailed Feb. 7, 2011.
European Search Report for EP 02752446 5pgs, Oct. 12, 2009.
European Examination Report for EP 037419405 4pgs, Jan. 11, 2010.

* cited by examiner

SUTURE DEVICE HAVING SELECTIVE NEEDLE ACTUATION AND RELATED METHOD

BACKGROUND OF THE INVENTION

The present invention relates to a method and apparatus for placing sutures in soft tissue with an ability to create a variable mattress stitch (e.g., to control the distance between sutures placed within tissue or to place a mattress stitch across torn tissue). The methods and devices described herein may also improve the ability to place a stitch or suture deeper within tissue when compared to conventional methods. Although methods and devices described herein make reference to arthroscopic repair of torn rotator cuffs, the principles of the devices and methods may be applied to any soft tissue application.

Traditional suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called "endoscopes", can be used in conjunction with specialized surgical instrumentation to detect, diagnose, and repair areas of the body that were previously only able to be repaired using traditional "open" surgery. In the past, there have been many attempts to simplify the task of driving a needle carrying suture through body tissues to approximate, ligate and fixate them. Many prior disclosures, such as described in U.S. Pat. No. 919,138 to Drake et al., employ a hollow needle driven through the tissue with the suture material passing through the hollow center lumen. The needle is withdrawn, leaving the suture material in place, and the suture is tied, completing the approximation. A limitation of these types of devices is that they are particularly adapted for use in open surgical procedures where there is ample room for the surgeon to manipulate the instrument.

Others have attempted to devise suturing instruments that resemble traditional forceps, such as U.S. Pat. No. 3,946,740 to Bassett. These devices pinch tissue between opposing jaws and pass a needle from one jaw through the tissue to the other jaw. Graspers then pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means "endoscopic surgery", or surgery performed using an endoscope. In conjunction with a video monitor, the endoscope permits the surgeon to remotely visualize the operative site. Operations using an endoscope are significantly less invasive when compared to traditional open surgery. Patients usually return home the next day, or in some cases, the same day of the endosurgical procedure. This is in contrast to standard open surgical procedures where a large incision divides the muscle layers and allows the surgeon to directly visualize the operative site. Patients may stay in the hospital for 5 to 6 days or longer following open surgery. In addition, after endosurgical procedures, patients return to work within a few days versus the traditional 3 to 4 weeks recuperative period at home following open surgery.

Access to the operative site using endosurgical or minimally invasive techniques is accomplished by inserting small tubes, known as trocars, into a body cavity. These trocars have a diameter of, for example, between 3 mm and 30 mm and a length of about 150 mm (6 inches). There have been attempts to devise instruments and methods for suturing within a body cavity through these trocar tubes.

Previous instruments for suturing within a body cavity are described in U.S. Pat. No. 4,621,640 to Mulhollan et al.; U.S. Pat. No. 4,935,027 to Yoon; U.S. Pat. Nos. 4,923,461 issued May 8, 1990 and U.S. Pat. No. 4,957,498 issued Sep. 18, 1990 to Caspari; U.S. Pat. No. 4,836,205 to Barrett; Garman et al in U.S. Pat. No. 5,499,991; U.S. Pat. Nos. 5,312,422 and 5,474,565 issued to Trott; the entirety of each of which is incorporated by reference.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally using instruments and techniques such as those previously described. This creates a simple stitch instead of the more desirable mattress or Mason-Allen stitch. Rather than thread the suture through trans-osseous tunnels which are difficult or impossible to create arthroscopically using current techniques, an anchor is driven into bone at a location appropriate for repair. The repair is completed by tying the cuff down against bone using the anchor and suture.

Early results of less invasive techniques are encouraging, with a substantial reduction in both patient recovery time and discomfort. However, as mentioned, this approach places only one loop of suture in the cuff for each anchor, reducing the fundamental strength of the repair. The knots in the tendon can be bulky and create a painful impingement of the tendon on the bone. This is because the knots end up on top of the cuff, in the sub-acromial space, and have the opportunity to rub on the acromion as the arm is raised. Because non-absorbable suture materials are used for these types of repairs, the suture and associated knots are not absorbed into the body, and hence provide a constant, painful reminder of their presence. The devices described herein are adaptable to effect the placement of a mattress stitch in grasped tissues by placing each end of the mattress stitch simultaneously, or allowing the medical practitioner to control the distance between the suture in the mattress stitch. Such a feature allows the mattress stitch to be placed across torn tissue or increase the span of the stitch. U.S. Pat. No. 5,431,666 to Sauer et al. discloses a suture instrument used to sequentially pull first and second suture lengths through tissue.

The devices and methods described herein are adaptable to place sutures precisely and controllably while making provision for needle retrieval when using endoscopic techniques by giving a medical practitioner the option of placing a mattress stitch of a pre-determined width or by allowing the medical practitioner to control the width of the stitch. In addition, variations of the methods and devices described herein incorporate features on the suturing device allowing for pulling tissue farther into the device to allow placement of the stitch deeper into the tissue.

Accordingly, although devices described herein are capable of arthroscopically creating a mattress stitch in soft tissue to increase the soft tissue pullout strength of the repaired tissue, the principles described may be applied to alternate stitching techniques or other tissue fixation techniques as well.

SUMMARY OF THE INVENTION

The present device and methods include an instrument that combines the function of both grasping the tissue and passing sutures through the tissue to form a stitch and preferably a mattress stitch.

In a general sense, the instrument includes a pair of grasping jaws that oppose each other along a line substantially perpendicular to the long axis of the instrument. The distal end of the instrument incorporates the fixed jaw, and proximal to that jaw is a moveable jaw that is controlled by the user via a lever on the handgrip.

In a preferred method of the present invention the instrument is inserted through a portal known as a trocar cannula. The portal is created by first making an incision in the skin, and then inserting a cannula through the incision to the repair site. The distal end of the instrument is inserted through the cannula under direct visualization from a second trocar cannula that has been previously inserted. The visualization is accomplished via an endoscope, of a type well known in the art. The instrument is inserted until the jaws reach, for example, torn rotator cuff tissue. In operation, the distal end of the grasper aspect of the instrument is positioned at the repair site underneath the tissue to be grasped. The moveable jaw pivots toward the stationary jaw by squeezing the handle lever. The handle lever moves inward by pivoting about a pivot pin. Once the appropriate section of tissue is isolated and grasped by the jaws, the lever may be locked in its closed position using a latch mechanism.

Once the surgeon is satisfied with the placement of the grasper on the grasped tissue, the surgeon can then deploy the suture needles to create a mattress stitch in the tissues, for example, the above-mentioned torn rotator cuff. In operation, the suture needles may be advanced through the grasped tissues by pulling on a second lever. The lever is directly connected to the needles via a connecting rod, and the lever is pulled against the force of a return spring. In turn, the connecting rod pushes a needle carriage, with suture needles held in the carriage.

The suture device may include a selecting member located within a housing of the device where the selecting member is rotatable and has an engagement surface that is axially moveable. The selecting member is rotatable between a plurality of positions including a central position, a first position, and a second position to selectively control deployment of one or both needles used to create the stitch. When in the central position, the engagement surface engages at least the first and second needles so that deployment of the lever moves both needles.

When rotated in a first position the engagement surface engages only the first needle, and when in the second position, the engagement engages only the second needle. Accordingly, the engaged needle is actuated by movement of the lever.

The suturing device can also have a selecting member that includes a stopping surface that is rotatable with the selecting member and axially fixed with respect to the housing, where when rotated in the first position, the stopping surface engages the second needle to prevent axial movement. It follows that when the device is in the second position the stopping surface engages the first needle to prevent axial movement. The selecting member may comprise a variety of structures. One such possibility is a split bushing configuration as shown herein. Furthermore, the proximal ends of the needle may have features that improve the ability of the stopping surface to prevent the needle from moving. An example of such features includes needles with shoulders, grooves, notches, etc., where such features may nest or fit into the stopping surface of the selecting member.

A further variation of the invention includes devices having a jaw that is of a shape to permit both rotational movement to trap tissue and axial movement to draw the tissue deeper into the device. Such a benefit allows the needles on the device to penetrate deeper into the tissue allowing for improved placement of the stitch. In such a case, the upper jaw includes a tissue grasping portion and a cam portion having a profile, where the tissue grasping portion and cam portion are located on substantially opposite ends of the jaw. The device will further include at least one jaw engaging surface proximal to the tissue receiving recess where axial movement of the jaw causes the cam portion to engage at least one of jaw engaging surface to further cause a rotational movement of the tissue grasping portion such that the tissue grasping portion moves axially and rotationally with respect to the tissue receiving recess.

The cam portion of the jaw may be of any profile depending upon the particular intended application or result. In most cases the cam portion will be an arcuate profile (whether a simple or compound curve.) Moreover, variations include cam portions having a non-arcuate profile.

The configurations described herein further allow for a method of suturing soft tissue comprising providing a suturing device having a tissue receiving recess and a jaw, where the jaw includes a tissue grasping portion and a cam portion having a profile, where the tissue grasping portion and cam portion are located on substantially opposite ends of the jaw. In order to secure tissue, the jaw is drawn proximally. This movement causes the cam portion of the jaw to move against engagement surfaces on the jaw to move the jaw rotationally relative to a tissue receiving recess. This action causes the jaw to engage the tissue in an arcuate motion and in an axial direction relative to the tissue receiving recess causing movement of the soft tissue into the tissue receiving recess. In order to create the suture, at least one needle advances through the soft tissue to engage a suture in the tissue.

The devices include features to allow the needles to penetrate tissue and then draw sutures back through the tissue. In one example, the needle carriage resides behind the proximal moveable jaw of the instrument, and, at the urging of the lever via the connecting rod, is able to move distally with the needles passing around the moveable jaw. As the carriage moves distally, the tips of the suture needles begin to clear the distal edge of apertures created in a more proximal portion of the stationary jaw, and begin to penetrate through the top of the grasped tissue and advance distally towards the more distal portion of the stationary jaw.

The stationary distal jaw incorporates two apertures that are adapted to receive the ends of the suture. Secondary open channels perpendicular to the suture apertures are configured with a specific geometry designed to direct the suture needles across the apertures containing the ends of the sutures. As the suture needles approach the end of their stroke, the distal ends of the needles have passed completely through the grasped tissues and begin to enter the secondary open channels in the stationary distal jaw.

At this point, any pull force being applied by the grasper on the grasped tissues is relaxed. Once the tissue is in a relaxed state, the jaws of the grasper are then opened. The handle lever is unlocked from the locking mechanism and returns to an open position due to the pull force exerted on it by means of a return spring. As the return spring pulls on the lever, it pivots about a pin.

To complete the pull out of the suture needles, it is necessary to pull on the grasper, and to remove it from the repair site. The instrument can be retracted back through the portal via the trocar cannula. As the instrument is removed from the suture site, the free ends of the suture are retrieved as well. This causes the suture to pass through the tissues at the puncture sites. As the suture is pulled through, the loop end of the suture is pulled snug against the underside of the tissues to form what is referred to as a mattress stitch. This process may be repeated as necessary, depending on the number sutures required for the particular procedure being undertaken.

Now it may be seen by those skilled in the art, that the combination of grasping tissues to be sutured and precisely placing a mattress stitch in the grasped tissues, while working through a trocar port, effects a significant advance in the art. Advantages of the present invention thus include providing an endoscopic instrument adapted for the grasping of tissues and creating a mattress stitch within those tissues, as well as the provision of a suturing instrument that allows for the reloading of additional sutures for placement of subsequent stitches. Additionally, the inventive system is advantageous in that it provides for controlling the spacing between the sutures in a mattress stitch as well as direct capture of the suture material subsequent to penetration of the tissue by the needles.

Another variation of the invention includes a suturing device, comprising a distal portion which is engaged with a length of suture, as well as a needle which is axially movable distally and proximally. A soft tissue receiving portion, preferably comprising a clamp having first and second jaws, wherein one of the first and second jaws is movable relative to the other to grasp soft tissue therein, is disposed proximally of the distal portion. A ramp portion for moving the needle radially inwardly and outwardly as the needle moves axially over the ramp portion is also provided.

A variation of the device includes a suture cartridge with a molded tip at the distal portion of the device for retaining the suture against the tip. Such a device may also include a ramp portion that comprises a radially outwardly sloping entrance ramp for moving the needle radially outwardly as the needle moves axially in a distal direction, as well as a radially inwardly sloping retraction ramp for moving the needle radially inwardly as the needle moves axially in a proximal direction.

There are a variety of needle configurations for use in the present invention in one example, the needle comprises a distal point, a proximal shaft, and a hook defining a suture holding area.

The hook portion of the needle is uniquely designed to provide a positive tactile indication as to when the suture has been capture within the suture holding area. This design includes a terminus of the hook, which is cantilevered proximally from a distal end of the needle. An optional bump on the needle in a location opposed to the hook terminus is provided, so that the hook terminus and the bump together may provide a tactile sensation to a user when suture passes thereover into the suture holding area.

In order to place a mattress stitch, a second needle, as well as a second ramp portion, is provided, so that a mattress stitch may be created.

The device may include a sheath, which is slidable relative to the needle, is provided for selectively covering each needle, particularly when the needle is being retracted proximally through the soft tissue, to prevent unnecessary damage thereto.

In another aspect of the invention, there is provided a needle for a suturing device, which comprises a distal point, a proximal shaft, and a hook defining a suture holding area. As noted above, the needle preferably further comprises a terminus of the hook, which is cantilevered proximally from a distal end of the needle, as well as a bump on the needle in a location opposed to the hook terminus.

The invention, together with additional features and advantages thereof, may best be understood by reference to the following description taken in conjunction with the accompanying illustrative drawing.

DESCRIPTION OF THE PREFERRED EMBODIMENT

Figure 1A:
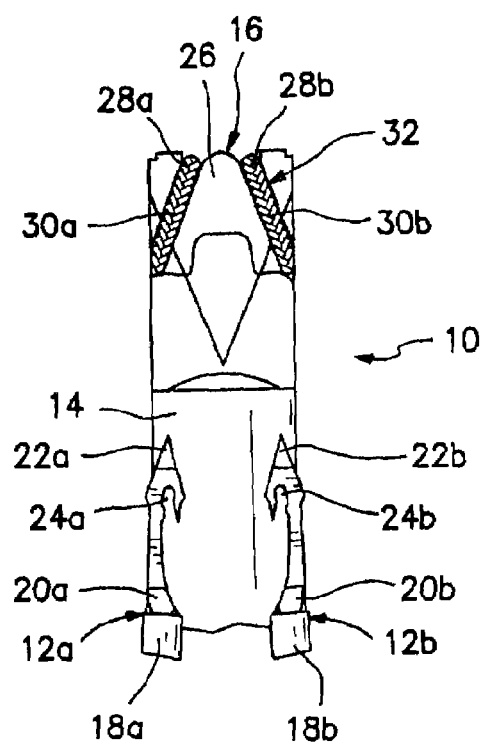
FIGS. 1A through 1E are detail plan views of the distal end of an instrument constructed in accordance with the principles of the present invention, illustrating the general structure and operation of the instrument.

The present invention relates to a method and apparatus for suturing of soft tissue at a surgical repair site. In one variation the invention uses an device that is a combination tissue grasper and suture placement device. Although the present invention is described primarily in conjunction with the repair of a torn rotator cuff, the apparatus and method could also be used in arthroscopic repair at other sites, such as the knee, elbow, hip surgery, and for other surgical techniques for securing suture in the soft tissues of the body.

A description of the basic functional elements of suture capture and retrieval, in accordance with the principles of the invention, follows.

FIGS. 1A through 1E illustrate an exemplary configuration of advancing needles 12a and 12b to engage a suture or ends of a suture 30a and 30b. *However, variations of the invention may include any number of configurations to retrieve the suture through tissue.*

FIGS. 1A through 1E illustrate a plan view of the distal end of a suturing device 10 that includes a pair of needles 12a and 12b, a lower jaw 14, and a suture cartridge 16. The needles 12a, 12b further include sliding tubes or sheaths 18a and 18b, needle shafts 20a and 20b, needle points 22a and 22b, and hooks 24a and 24b. The suture cartridge 16 comprises a molded tip 26 with grooves 28a and 28b, into which the two ends 30a and 30b of a length of suture are threaded.

Figure 1B:
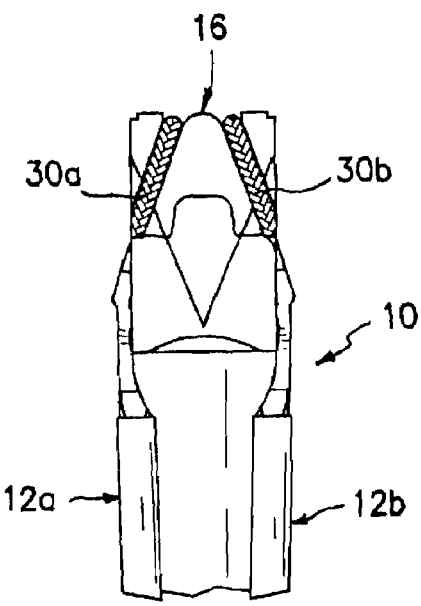

Referring to FIG. 1B, the needles 12a, 12b are advanced distally toward the suture cartridge 16 in preparation for capture and retrieval of the two ends 30a, 30b of the length of suture. It is to be understood that the entire length of the suture which includes the two ends 30a, 30b is not seen in this illustration. The loop of suture between the two ends 30a, 30b trails beneath the distal end of the suturing device 10 and is thus not visible. It will be described more fully later how the capture of the two ends of a suture can be used to create what is known in the art as a mattress stitch.

Figure 1C:
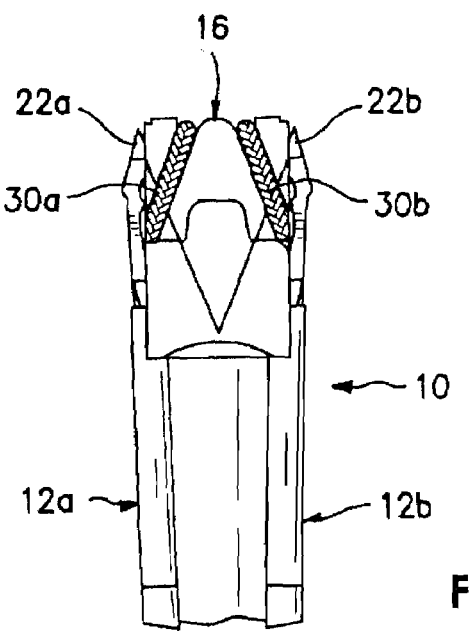
Figure 1D:
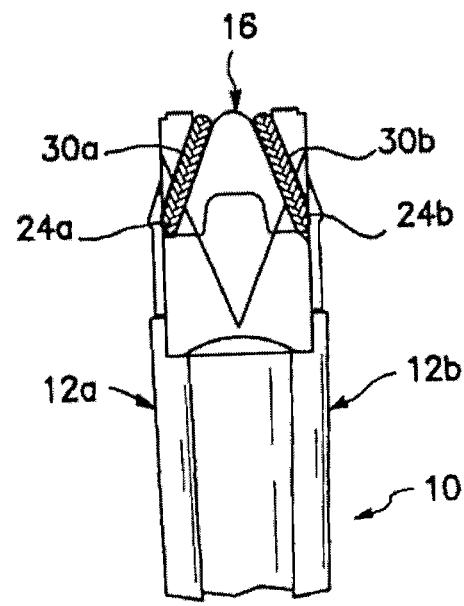
Figure 1E:
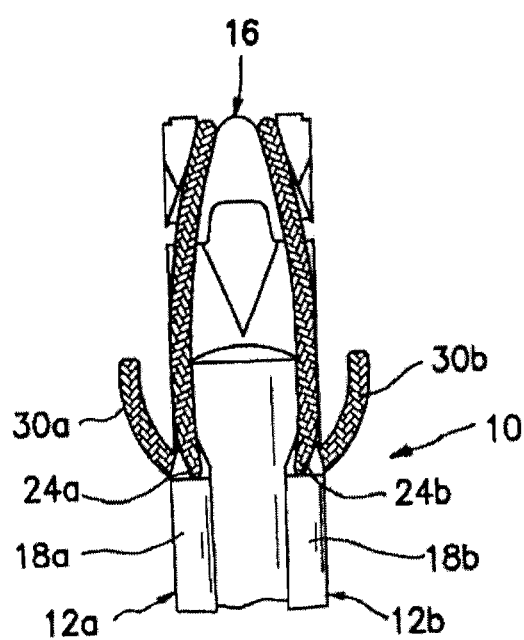

Referring now to FIG. 1C, it may be seen that the needles 12a, 12b are further advanced distally toward the suture cartridge 16 and past the two ends 30a, 30b of the suture, placing the hooks 24a, 24b in position past the two suture ends 30a, 30b in preparation for capture. As it may be seen in FIG. 1D, as the needles 12a, 12b are retracted proximally, the hooks 24a, 24b engage the two suture ends 30a, 30b and capture them for retrieval. As the needles 12a, 12b are further retracted proximally as shown in FIG. 1E, the sliding tubes 18a, 18b, held stationary by frictional forces exerted by tissue (not shown), cover the hooks 24a, 24b and assist in the engagement of the two ends 30a, 30b.

Figure 14:
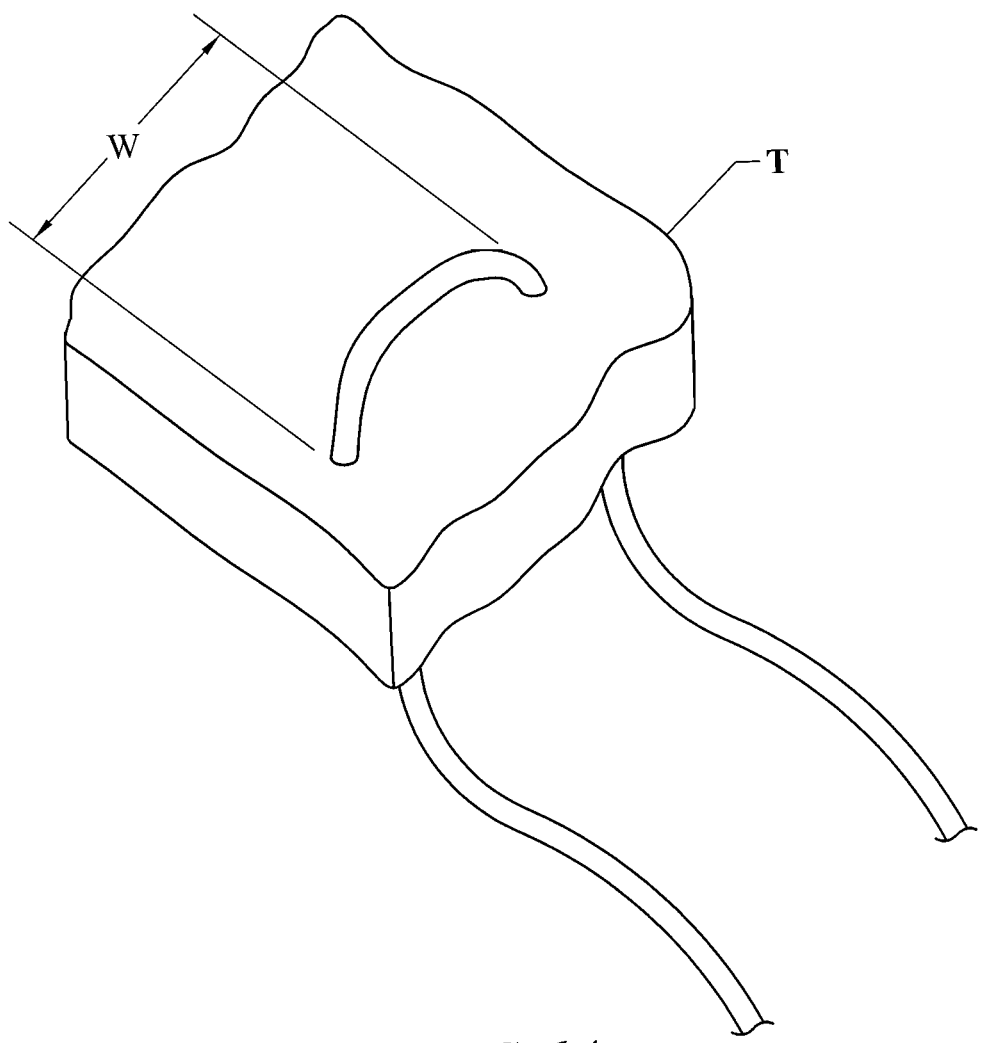
FIG. 14 shows a stitch placed in a tissue.
Figure 15A:
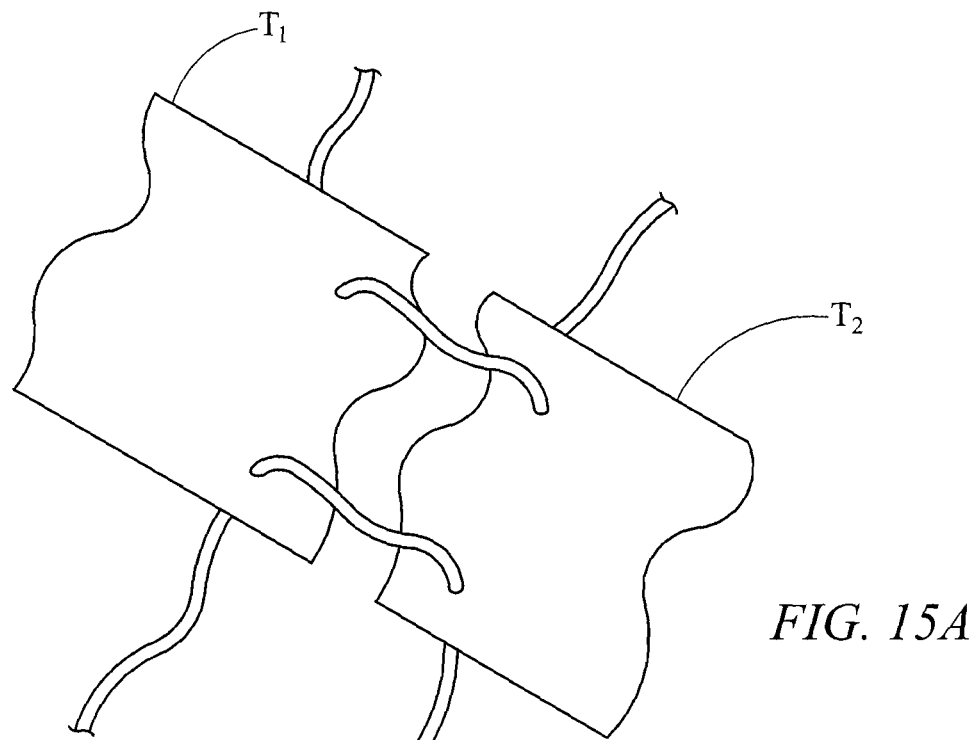
FIGS. 15A through 15B show a pair stitches placed across a tear.
Figure 15B:
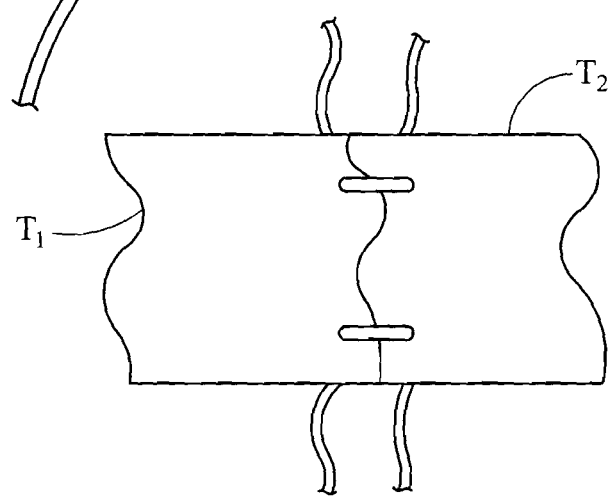
Figure 16:
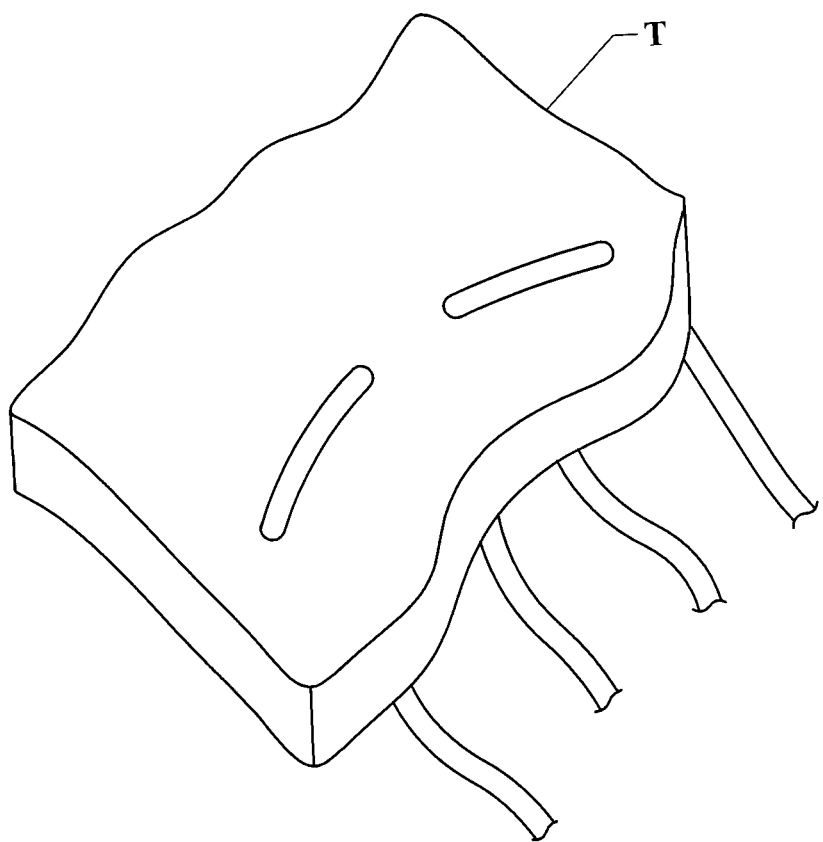
FIG. 16 shows a row of stitches placed in a tissue.

As discussed above, it may be desirable to advance the needles selectively. In such a case, one needle may be advanced through tissue to place a single suture. Subsequently, the medical practitioner can re-adjust the device on the soft tissue for placement of the second suture in the mattress stitch. Doing so allows for a mattress stitch to have a width (W) to be independent of the spacing of the needles (see, e.g., FIG. 14), or to be placed across a tear separating tissue portions $T_1$, $T_2$ (e.g., FIGS. 15A-15B). It is also desirable that the device provide the option to place a mattress stitch by actuating both needles simultaneously. Additionally, multiple sutures may be placed in a tissue as shown in, for example, FIG. 16. Indeed, a row(s) of stitches (e.g., mattress stitches) may be placed in a tissue to bolster fixation.

Figure 2A:
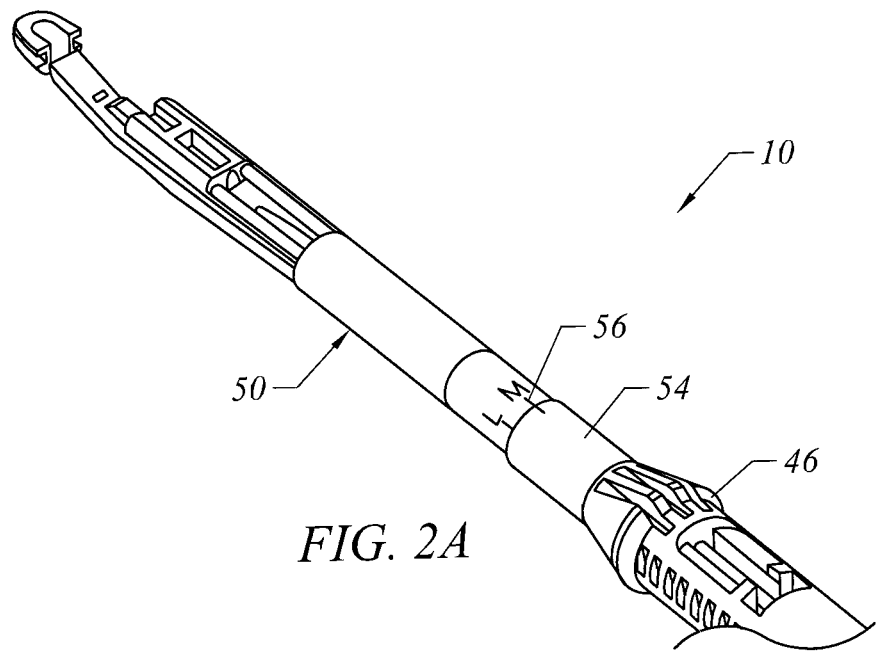
FIGS. 2A through 2F illustrate an example of a suture device having a selecting member to engage one or more needles on the device.

FIG. 2A illustrates an example of a variation of a suturing device 10 in accordance with the invention. To illustrate the selectivity of the needle 12 actuation, the device 10 is shown without sutures or a moveable jaw member.

As illustrated the device 10 includes a housing 50 having a distal portion 52 that engages the suture (e.g., via a suture cartridge or other means of affixing the suture to the device). The distal portion 52 also includes an area (typically referred to as the tissue receiving recess) for securing the tissue so that the distal ends of the needles 12 may penetrate the tissue to secure sutures within the tissue.

The housing 50 may be coupled to a handle portion 46. The handle portion 46 may be of a similar or the same design as those typically used in conventional suturing devices as discussed above. For example, such a handle may have a stationary grip with a moveable needle deployment lever. Such handle portions include a needle deployment member or trigger to effectuate closing of the jaws and subsequent axial movement of the needles to secure the tissue.

FIG. 2A also shows the device 10 as having a rotatable member 54 (e.g., a knob, dial, or similar such component). As discussed below, the rotatable member 54 is engaged with the needle actuation mechanism to selectively engage one or both needles. For ease of use, the device 10 may include markings 56, 58 to indicate the position of the actuation mechanism. In the illustrated case, the marking 56 indicates that the device is in the central or medial position. Again, as discussed below, in this position, the device engages both needles for deployment into tissue. The rotatable member 54 may be located on the handle portion. Alternatively, the rotatable member 54 may be located on the needle housing 50.

Figure 2B:
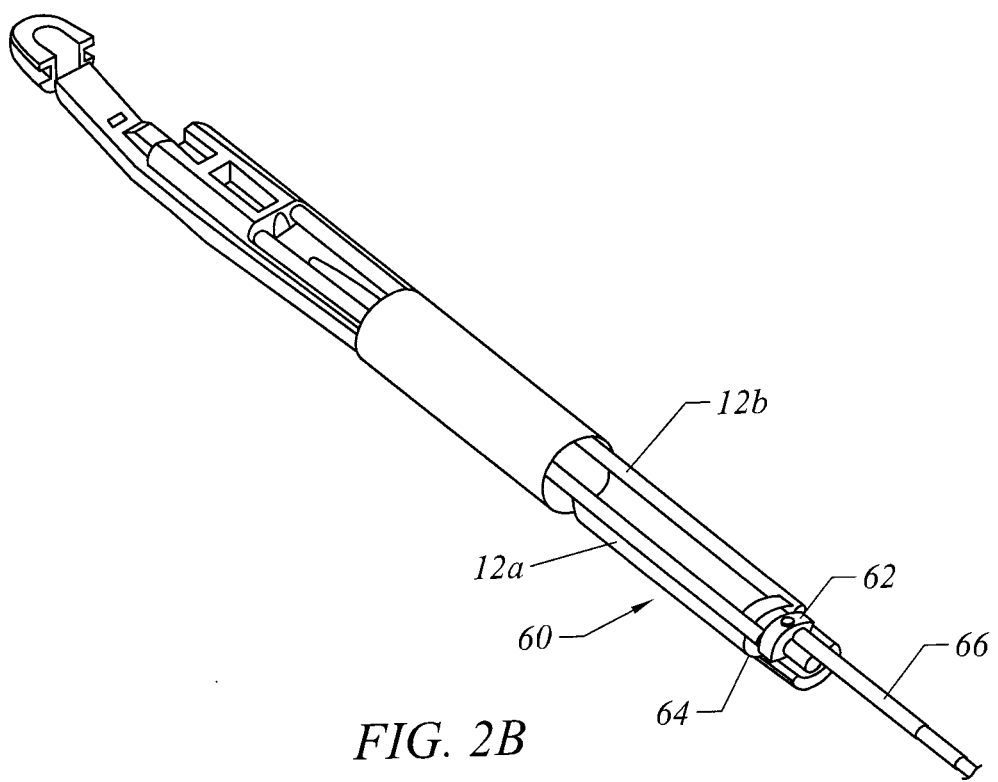

FIG. 2B illustrates another view of the device 10 with part of the housing and handle removed. As illustrated, the proximal ends of the needles 12 engage a selecting member 60. In the illustrated variation, the selecting member 60 comprises a number of bushings. However, it is understood that variations may be employed so long as they produce the same effect as described herein.

FIG. 2B shows the proximal ends of the needles 12 engaged with an engagement surface 62. Again, in this variation, the engagement surface 62 comprises a first half of a split bushing. As described below, the engagement surface 62 will be coupled to the trigger portion of the handle (in this case via a shaft 66) so that actuation of the trigger portion axially moves the engagement surface 62 along with the needles that are coupled thereto. The selecting member 60 allows for axial movement of the engagement surface 62 but in most variations the selecting member 60 is prevented from axial movement (e.g., by being affixed to a stationary portion of the handle).

Variations of the device 10 may further include a stopping surface 64 on the selecting member 60. In this variation, the stopping surface 64 is located on a second half of the split bushing. As described below, the stopping surface 64 may be used to secure a needle and prevent its movement as an adjacent needle advances into the tissue. As noted above, the variation shown in FIG. 2A configured in a central or medial position. In such a position, the engagement surface 62 engages both of the needles 12 while the stopping surface 64 is not in engagement with either needle.

Figure 2C:
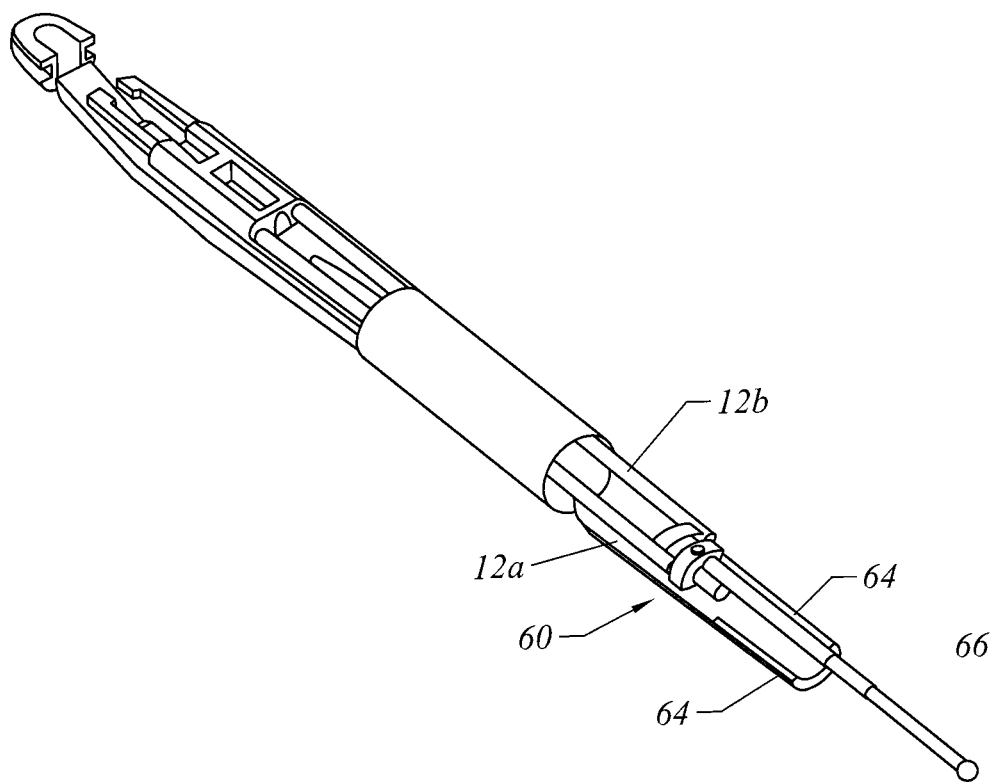

FIG. 2C illustrates the engagement surface 62 moving distally when engaged with both needles 12. As illustrated, the stopping surface 64 of the selecting member 60 remains stationary. Ultimately, the axial movement of the needles 12 causes the distal ends to advance across the tissue receiving recess 48.

Figure 2E:
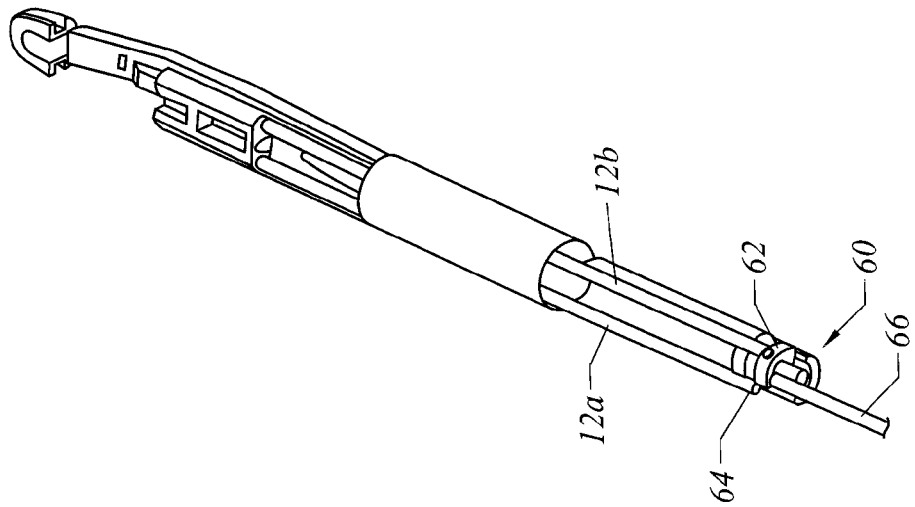
Figure 2D:
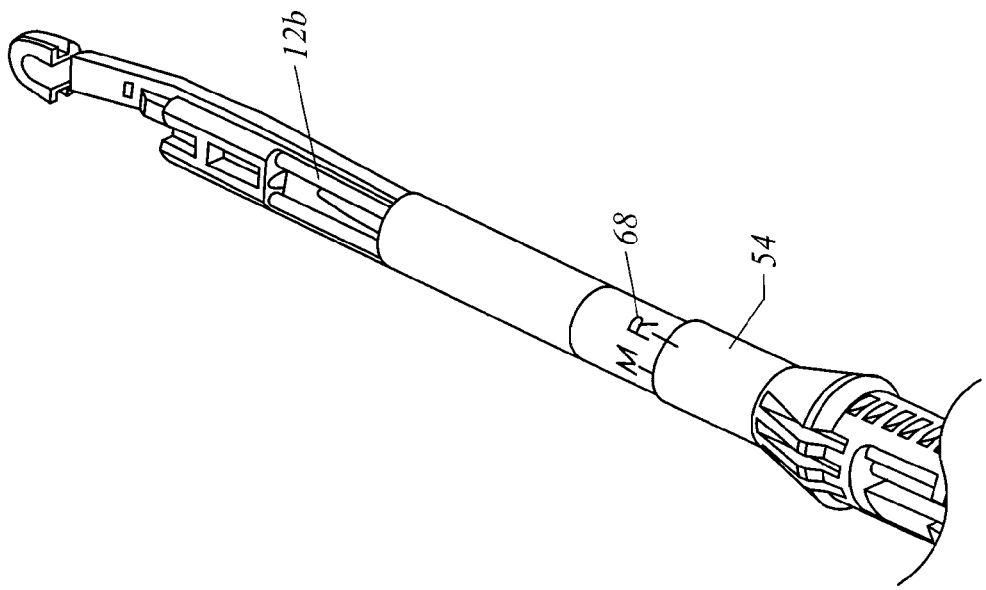

FIG. 2D illustrates an view of the device 10 in which the rotatable member 54 is configured to select a single needle 12. In this variation, the rotatable member 54 and marking 68 indicate that the device is engaging the right needle as shown by the corresponding indicator pointing to the right marker "R" 68.

FIG. 2E illustrates another view of the device 10 with part of the housing and handle removed. As shown, rotation of the rotating member 54 rotates the selecting member 60 so that the engagement surface 62 disengages the left needle 12a.

As shown in the above figures, the engagement surface 62 can have a cross sectional area less than that of the cross sectional area of the passage through the housing. Accordingly, rotation of the engagement surface 62 permits an orientation of the engagement surface 62 that passes over the disengaged needle (in this case 12a) as the engagement surface moves axially. As an additional measure to prevent unwanted movement of a particular needle, a variation of the device uses a stopping surface to engage the stationary needle. For example, as shown in FIG. 2E, the stopping surface 64 can engage the proximal end of the left needle 12a to prevent any axial movement.

Figure 2F:
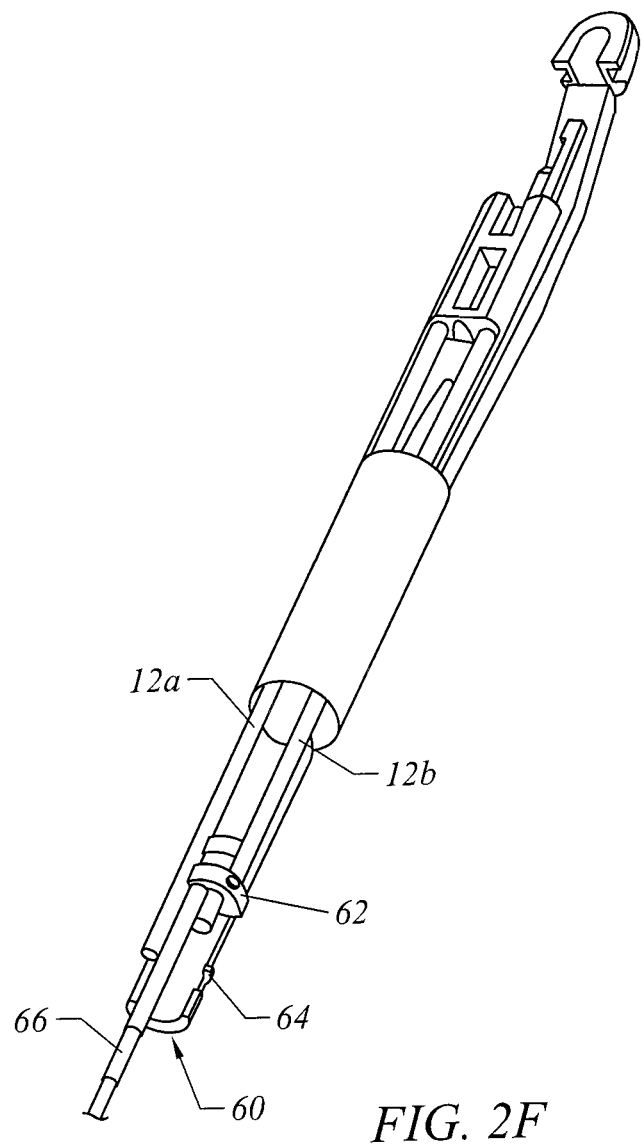

FIG. 2F, shows selective advancement of the right needle 12b. As shown, the shaft 66 remains in contact with the engagement surface 62 so that advancement of the shaft 66 ultimately axially advances the engaged right needle 12b. As shown, the proximal ends of the needles may include grooves, protrusions, or other features to permit improved nesting against the stopping surface 64 of the selecting member 60.

Although not illustrated, after the medical practitioner deploys the needle through tissue and withdraws the engagement surface. The rotatable member may be adjusted to couple the engagement surface 62 with the left needle 12 for eventual deployment into tissue.

Figure 3A:
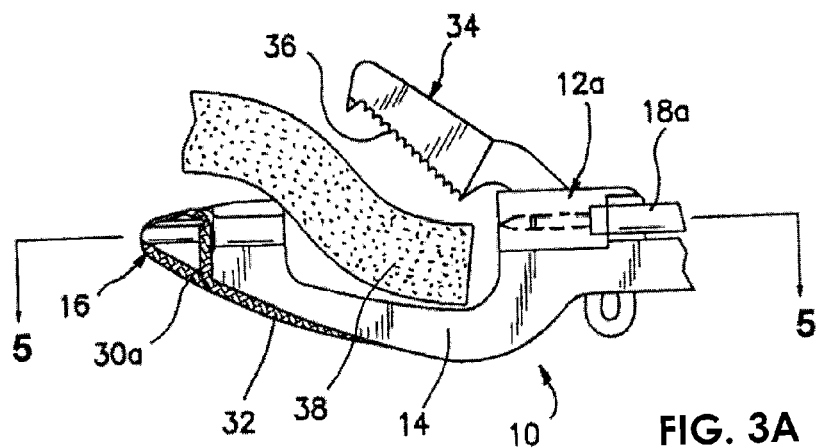
FIGS. 3A through 3E are detail side views of the distal end of the instrument of FIGS. 1A through 1E, which again illustrate the general structure and operation of the present invention.
Figure 3B:
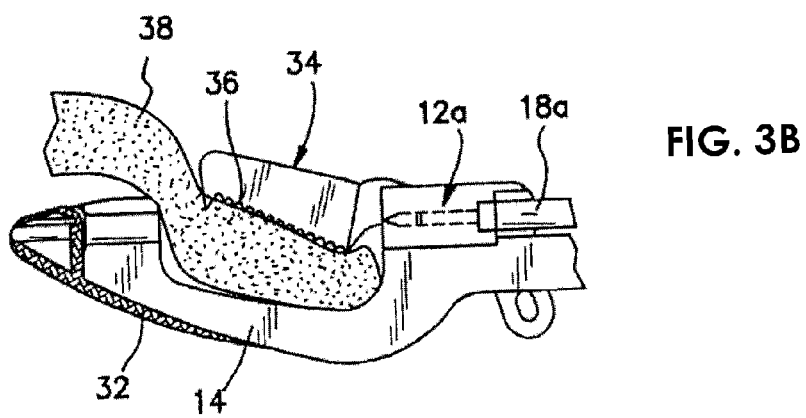
Figure 3C:
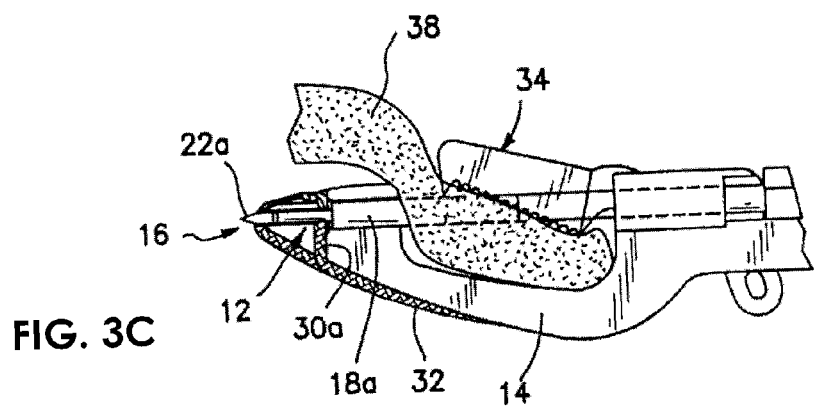

FIGS. 3A through 3E provide an example of placement of a stitch, and more specifically, a mattress stitch, in soft tissues. Referring now to FIGS. 3A through 3E, there may be seen detail side views of a suturing device 10 a. The device 10 includes the suture end sections 30a, 30b of a single strand of suture 32, and an upper jaw 34, which includes teeth 36. Referring now to FIG. 3B, soft tissue 38 is introduced into the space between the upper jaw 34 and the lower jaw 14. By means of a mechanism not discussed or shown herein, but of a type well known to those skilled in the art, the upper jaw 34 is pivoted about an axis, causing it to clamp or grasp the soft tissue 38 and immobilize it between the teeth 36 of the upper jaw 34 and the lower jaw 14. Referring now to FIG. 3C, it may be seen that the needles 12 have been advanced distally through the soft tissue 38 and in engagement with the suture cartridge 16 with the needle points 22a, 22b advancing beyond the suture ends 30a, 30b.

Figure 3D:
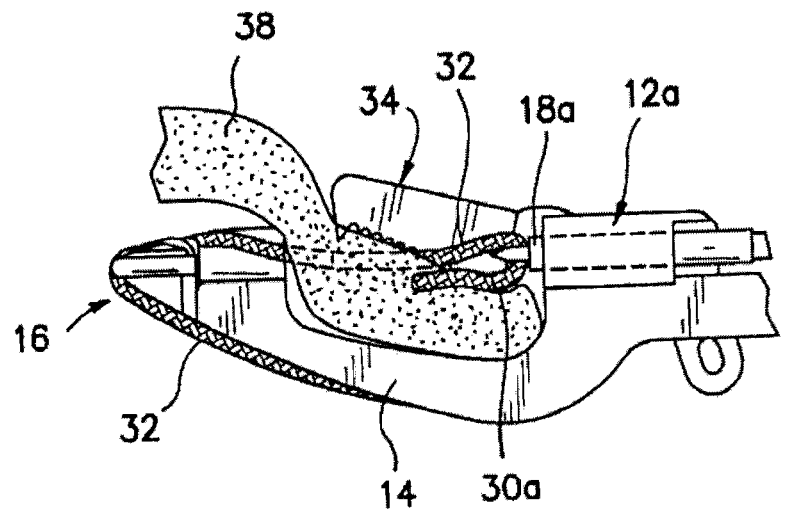
Figure 3E:
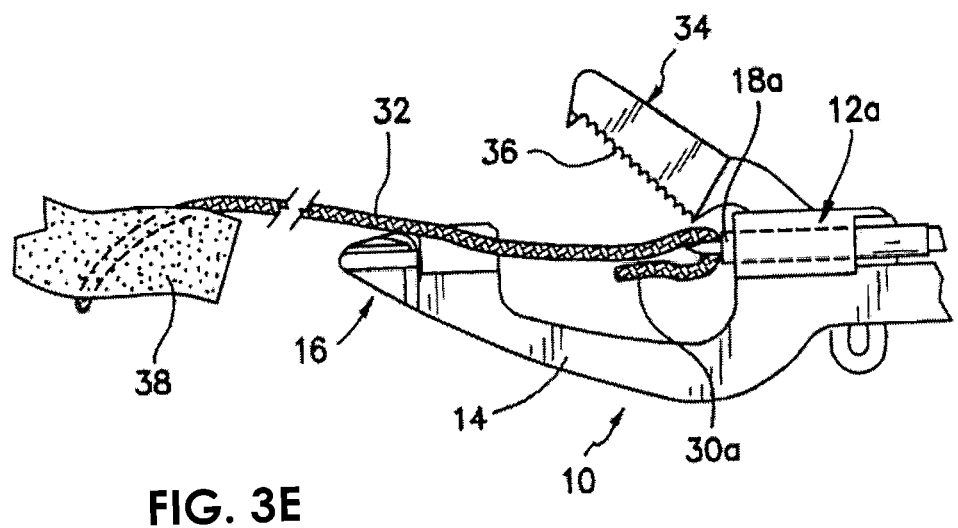

It is to be understood that in this view, only one needle 12a of the two needles 12a 12b may be visualized, but that a concomitant needle 12b may also penetrate the tissue along a substantially parallel path depending upon the configuration selected by the medical practitioner. As seen in FIG. 3D, the needle 12a is retracted proximally, trailing the suture 32 by virtue of having captured the suture ends 30. In this way, the suture 32 is placed through the soft tissue. Referring to FIG. 3E, it may be seen that the upper jaw 34 has been pivoted away from the soft tissue 38, allowing the suturing device 10 to be retracted away from the soft tissue 38, pulling the suture 32 completely through the soft tissue 38. The result of this action is the placement of a mattress stitch in the grasped tissues in a manner similar to that previously described.

Figure 4A:
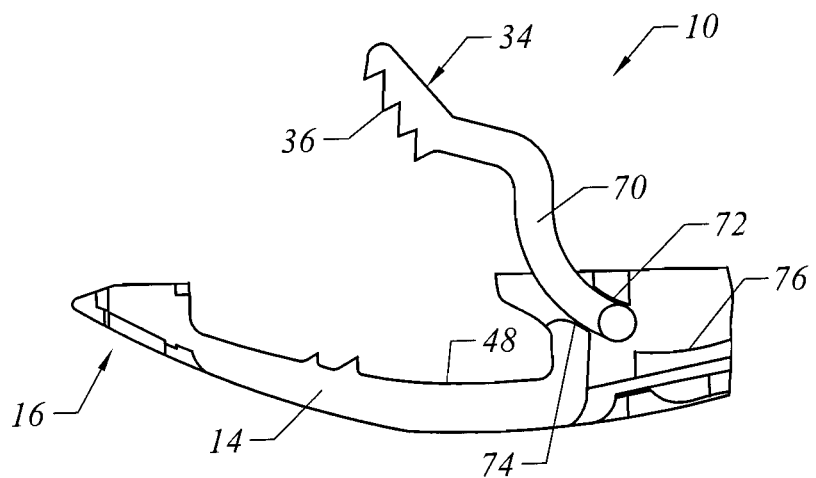
FIGS. 4A through 4D illustrate a variation of an upper jaw for use with a suture device where the upper jaw includes a cam portion to facilitate both axial and rotational movement to draw tissue deeper into a cavity of the device.

FIG. 4A illustrates another variation of an upper jaw 34 for use with the devices 10 described herein. In this variation, the upper jaw 34 has a tissue grasping portion or teeth 36 and a cam portion 70, where the tissue grasping portion 36 and cam portion 70 are located on substantially opposite ends of the jaw 34. As illustrated, the profile of the upper jaw 34 may have an additional curved profile between the tissue grasping portion 36 and the cam portion 70. In this example, the profile allows for the tissue grasping portion 36 to move closer to the bottom of the tissue receiving cavity 48 when the jaw 34 is closed.

As discussed below, the illustrated jaw 34 configuration shown in FIG. 4A, allows the jaw 34 to withdraw tissue farther into the tissue receiving cavity 48. To accomplish this movement, the cam portion 70 engages one or more jaw engaging surfaces 72, 74, 76 located on the device and proximal to the tissue receiving cavity 48.

Accordingly, as the jaw moves in a proximal direction, the cam portion 70 of the jaw engages a surface, in this example 72 and 76 (and hereafter referred to as jaw engaging surfaces). The engagement of the cam portion 70 against the jaw engaging surfaces ultimately causes a rotational movement of the tissue engaging portion 36 as well as an axial movement in the proximal direction relative to the tissue receiving cavity 48. This motion not only pulls the tissue into the tissue receiving cavity, but it also pulls tissue in a proximal direction within the cavity 48. As a result, the needles (not shown) are better able to penetrate deeper into the tissue when actuated.

Figure 4B:
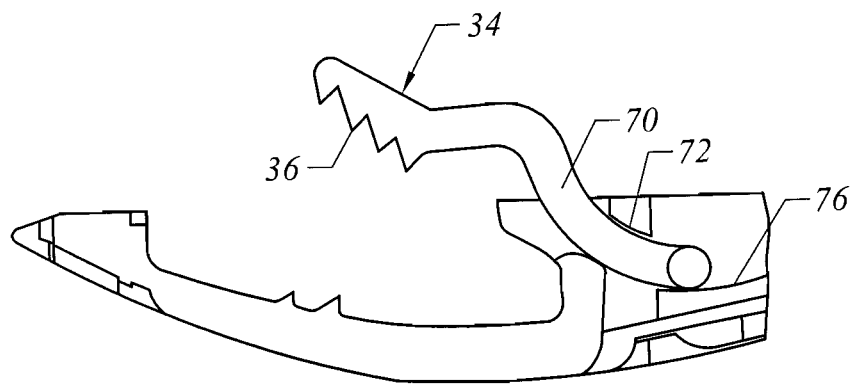
Figure 4C:
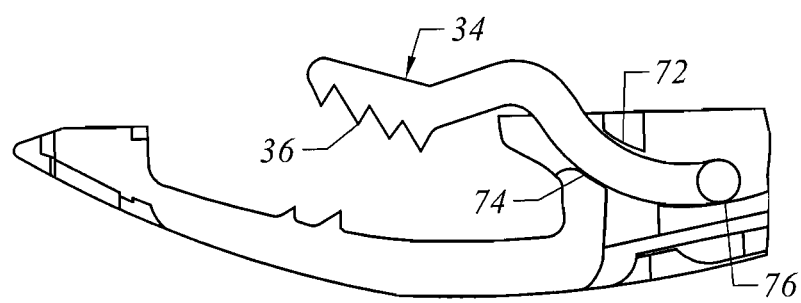
Figure 4D:
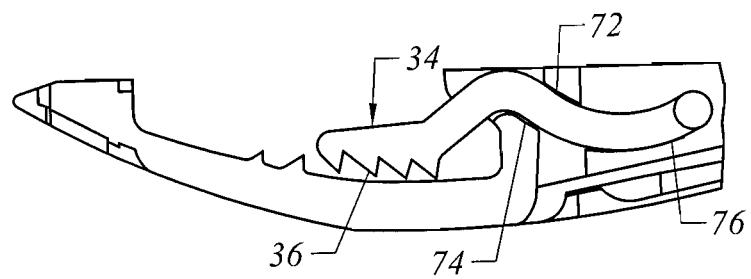

FIGS. 4B-4D illustrate movement of the tissue grasping portion as it enters the tissue receiving cavity 48 and simultaneously moves in a proximal direction. Naturally, distal movement of the jaw 34 causes urging of the cam portion 70 against the jaw engaging surface 74 to move the jaw in an opposite direction to release tissue.

Although not illustrated, the jaw 34 may be connected to any type of advancement/retraction structure to allow the medical practitioner to actuate the jaw 34. As shown in FIGS. 4A-4D, the tissue receiving cavity 48 may also include protrusions or teeth 78 to assist in retaining the tissue within the tissue receiving cavity as needles advance through the tissue.

The shape or profile of the cam portion 70 of the jaw is not limited to that shown. The shape may be chosen as a simple curve, compound curve, or other profile as required by the particular application.

The devices described above may incorporate characteristics, geometries and interfaces between parts that combine to optimize the performance of the suture capture mechanism. Such features are shown by way of example in FIGS. 3A through 4D, However, the variations of the invention herein may be combined with any type of suture capturing mechanism.

Figure 5A:
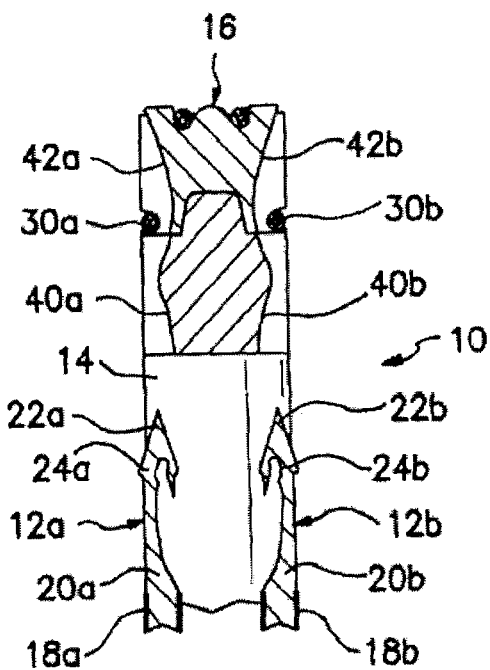
FIGS. 5A through 5E are cross sectional plan views of the distal end of the instrument of FIGS. 1A through 1E, showing the relationship between the body structure and the needle geometry.
Figure 5B:
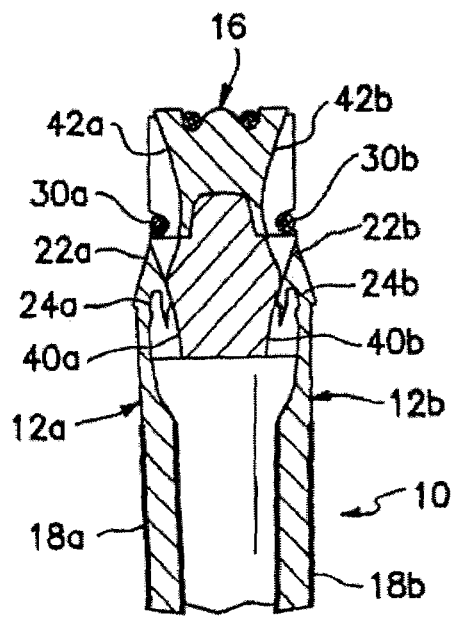
Figure 5C:
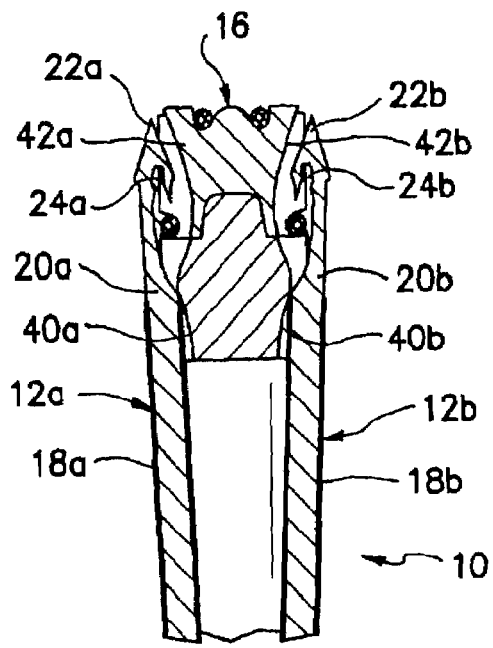

FIGS. 5A through 5E depict cross sections taken along the lines 5-5 in FIG. 2A. Referring now to FIG. 5A, there is seen the suture device 10 which includes the needles 12a, 12b, lower jaw 14, suture cartridge 16, and suture ends 30a, 30b. The upper jaw 34 and the soft tissue 38 have not been shown in these figures for clarity. It is possible to now see entrance ramps 40a, 40b and retraction ramps 42a, 42b that are in the path of the needles 12a, 12b. By referring to FIG. 5B, it may be seen that as the needles 12a, 12b move distally in the direction of the suture cartridge 16, the tips of the needles 12a, 12b engage the entrance ramps 40a, 40b. The engagement with the entrance ramps 40a, 40b deflects the needles 12a, 12b such that the needle points 22a, 22b are directed over and away from the suture ends 30a, 30b, preventing the needle points 22a, 22b from piercing or otherwise damaging the suture ends 30a, 30b. Further distal movement of the needles 12a, 12b, as shown in FIG. 5C, allows the hooks 24a, 24b to be disposed distally of the suture ends 30a, 30b and in position to capture the suture upon retraction. It is to be noted that, at this juncture, the sliding tubes 18a, 18b have entered the area of the entrance ramps 40a, 40b, and have begun to ride up the entrance ramps 40a, 40b, thus further deflecting the needles 12a, 12b.

Figure 5D:
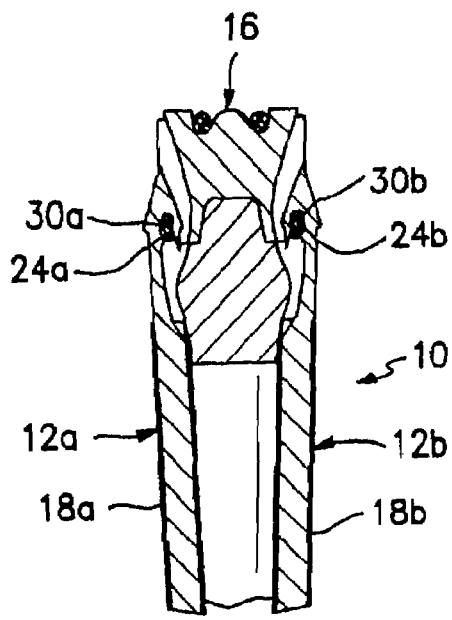
Figure 5E:
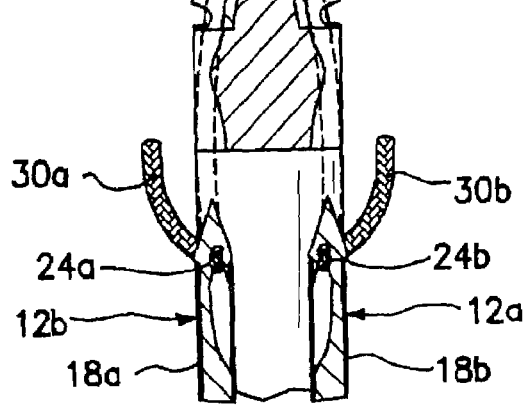

Referring now to FIG. 5D, it may be appreciated that as the needles 12a, 12b are retracted proximally, the needle hooks 24a, 24b ride down the retraction ramps 42a, 42b and under the suture ends 30a, 30b, thereby capturing the suture ends 30a, 30b in the hooks 24a,b, and allowing the suture ends 30a, 30b to be peeled away from the suture cartridge 16 and retracted proximally. It may also be appreciated that as the needle shafts 20a, 20b retract, the sliding tubes 18a, 18b remain motionless in the soft tissue (not shown), allowing the sliding tubes to cover the gap made by the hooks 24a, 24b and allowing smooth passage through the tissue. This retraction may be appreciated by comparing the position of the sliding tubes 18a, 18b relative to the hooks 24a, 24b in FIGS. 5D and 5E. Once the sliding tubes 18a, 18b have covered the gap, they retract along with the needle shafts 20a, 20b back through the soft tissue 38.

Figure 6:
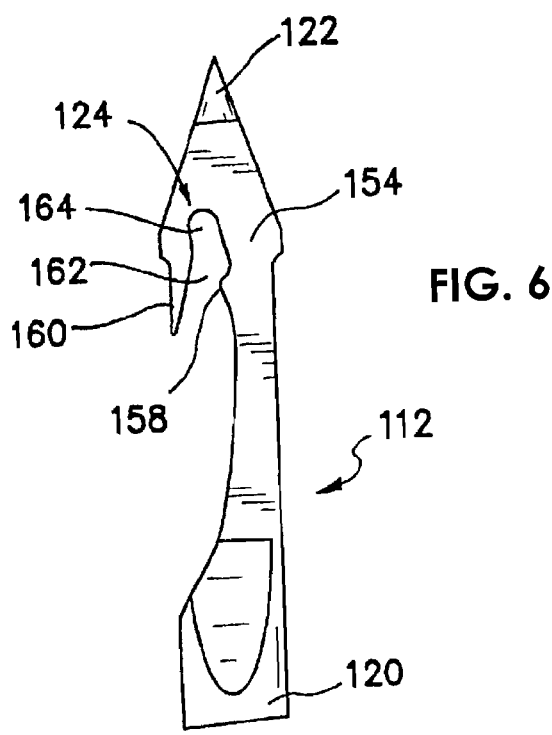
FIG. 6 is a detailed view of a needle of the present invention.
Figure 7:
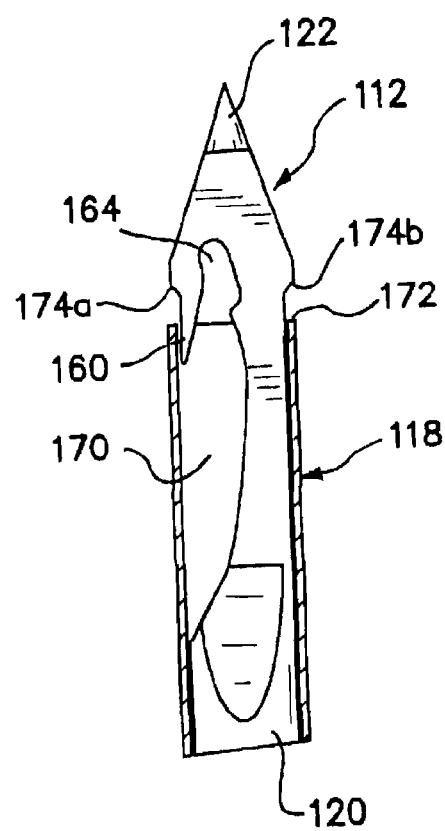
FIG. 7 is a detailed view of the needle of FIG. 5 with an associated sleeve.

A more complete and detailed description of the construction and operation of the needles may be understood by referring to FIGS. 6, 7, where there may be seen, in isolation, a needle 112 constructed in accordance with the principles of the present invention, wherein like elements to those described in prior embodiments bear like reference numerals, preceded by the numeral 1.

The needle 112 thus includes a needle shaft 120, and a flattened distal portion 154. The flattened distal portion 154 of the needle 112 includes a hook 124, comprising a bump 158, a hook terminus 160, a hook entrance 162, a suture holding area 164, and a needle point 122. The specific geometry of the needle 112 that is described herein is to be understood as being representative of a family of configurations that embody the design parameters that are now to be described. For instance, the needle point 122 shown herein is a beveled cutting point, but may be, for example, a conical or trocar point. Further, the position of the bump 158 may be on the opposite side of the hook entrance 162. These, and other nuances will be discussed in more detail further below.

When the needle 112 has been introduced through soft tissue (not shown) and has been driven past the suture to be captured as previously illustrated in FIGS. 1C, 2C, and 5C and has begun to be retracted back through the soft tissue, the hook terminus 160 rides along one of the retraction ramps 42a, 42b and underneath one of the ends 30a, 30b of the suture, thus forcing the suture through the hook entrance 162 and past the bump 158 into the suture holding area 164. The hook terminus 160, being cantilevered, has some flexibility, and opens slightly as the suture passes the bump 158, creating a subtle tactile sensation as the suture seats in the suture holding area 164. The suture holding area 164 is sized so that its cross sectional area is slightly smaller than the cross sectional area of the suture it is designed to capture, thus creating some compression of the captured suture by virtue of the spring loading provided by the above described deformation of the hook terminus 160.

It is important to understand that in variations of the invention using this particular configuration of needle 112, the needle is configured to capture a section of suture substantially near one of the ends of the suture. As such, and because the needle is not capturing the suture near the center of the strand of suture where the drag on both legs of the suture as it is retracted through the tissue would be equalized, it is important to prevent the suture from migrating in or through the suture holding area 164. It is also important to secure the suture in the needle while the instrument is being withdrawn, to form and complete, for example, a mattress stitch. Therefore, the combination of deformation, tactile sensation, and compression conspires to hold the suture securely.

Another aspect of the presently described needle configuration is the mechanism described to effect smooth passage of the needle hook with captured suture back through the soft tissue as the needles are retracted. To that end, FIG. 7 illustrates the needle 112 together with a sliding tube 118, which includes an inner lumen 170, and a lumen opening 172. The sliding tube 118 is dimensioned so that the needle shaft 120 may slide freely through the inner lumen 170, but does not allow sufficient clearance between the inner lumen 170 and the needle shaft 120 to permit tissue to enter the lumen opening 172. As the needle 112 is retracted through the tissue as previously described, the sliding tube 118 remains motionless, closing the opening formed by the hook terminus 160 and the suture holding area 164. The lumen opening 170 ultimately bottoms out against needle shoulders 174a, 174b, and assists in pinching and holding any suture that may be captured in the needle hook 64.

Figure 8:
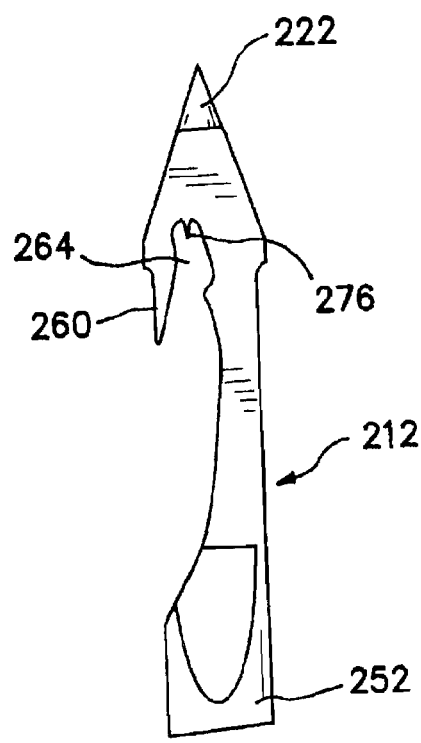
FIG. 8 is a detailed view of an alternative embodiment of a needle of the present invention.

An alternative needle embodiment is illustrated in FIG. 8, wherein like elements to those of the embodiment of FIGS. 6 and 7 are denoted by like reference numerals, except that they are increased by 100. In this embodiment, there may be found a needle 212 that has features similar to that of the needle 112 described above. In this embodiment, a barb 276 is included as part of the suture holding area 264, and is configured to penetrate the suture weave and assist in immobilizing the suture.

Figure 9:
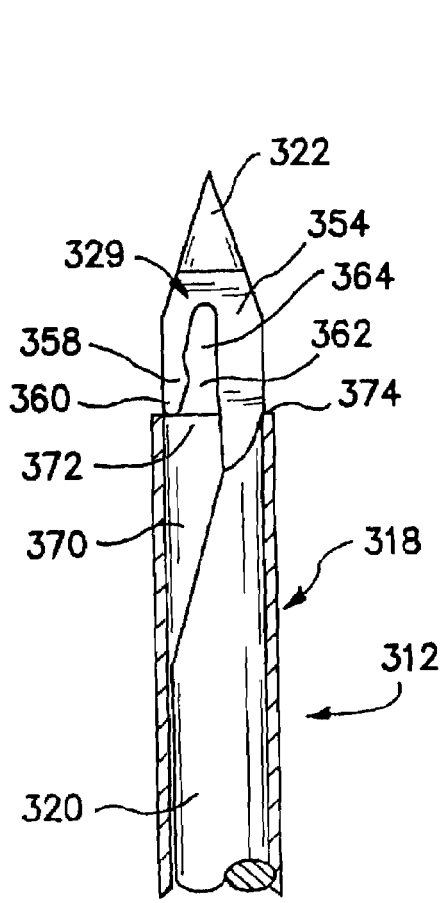
FIG. 9 is a detailed view of another alternative embodiment of a needle of the present invention.
Figure 10:
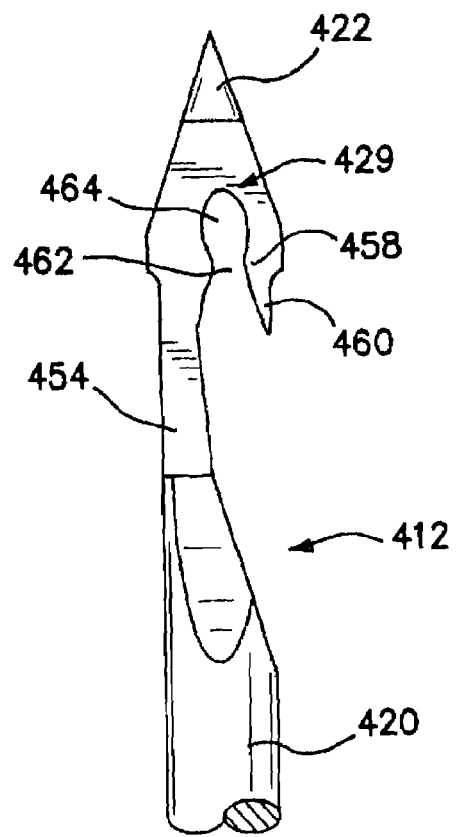
FIG. 10 is a detailed view of still another alternative embodiment of a needle of the present invention.
Figure 11:
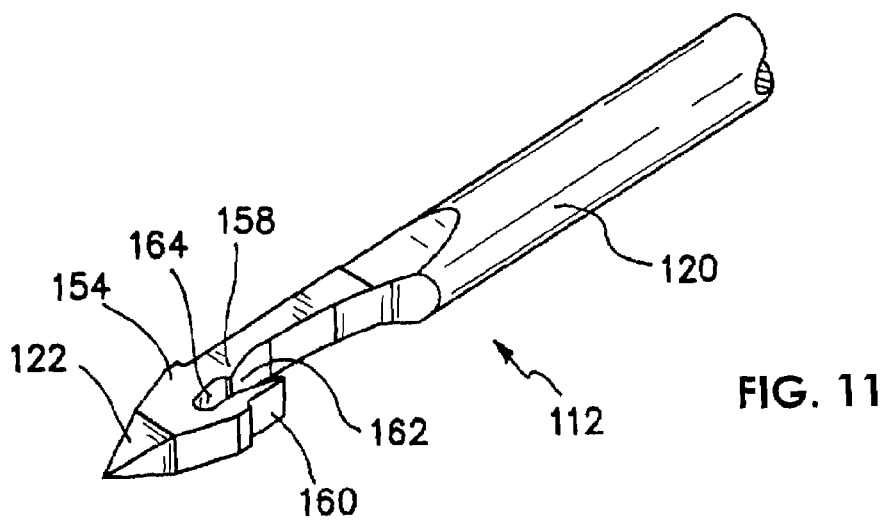
FIG. 11 is a perspective view of the needle of FIG. 6.

FIGS. 9 and 10 illustrate additional embodiments of the needle, and as above, like elements are denoted by like reference numerals, except in the case of FIG. 9, the labels are increased by 100 respective to FIG. 8, and in FIG. 9, increased by 200 respective to FIG. 8.

Accordingly, in FIG. 9 there may be seen a needle 312 that includes a needle shaft 320, and a flattened distal portion 354. The flattened distal portion 354 of the needle 312 includes a hook 324, comprising a bump 358, a hook terminus 360, a hook entrance 362, a suture holding area 364, and a needle point 322. The needle 312 is illustrated along with a sliding tube 318 which includes an inner lumen 370, and a lumen opening 372. It is important to note from this illustration that the sliding tube 318 may bottom out on the end of the hook 324 as opposed to covering it as previously described. Also, the bump 358 is shown here on the opposite side of the hook entrance 362.

Referring now to FIG. 10, there may be seen a needle 412 that includes a needle shaft 420, and a flattened distal portion 454. The flattened distal portion 454 of the needle 412 includes a hook 424, comprising a bump 458, a hook terminus 460, a hook entrance 462, a suture holding area 464, and a needle point 422. This embodiment is provided to illustrate that the suture holding area 464 may take on a shape different from that previously disclosed.

Figure 12:
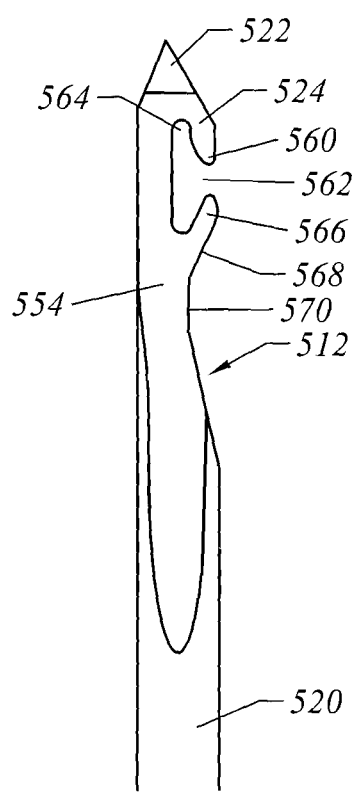
FIG. 12 is a detailed view of another alternative embodiment of a needle.
Figure 13:
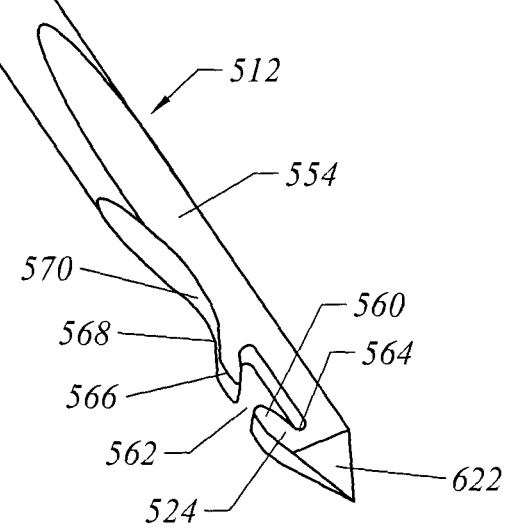
FIG. 13 is a perspective view of the needle of FIG. 12.

FIGS. 12-13 illustrate another embodiment without a sliding tube(s) 318. In particular, FIGS. 12 and 13 show a needle 512, including a needle shaft 520, and a flattened distal portion 554. The flattened distal portion 554 of the needle 512 includes a hook 524, comprising a hook terminus 560, a hook entrance 562, a suture holding area 564, and a needle point 522. Proximal to the hook entrance 562 is a tissue bumper 566 which includes a sloped bevel 568 and a ramp relief 570.

These structures cooperate to allow the needle 512 to effectively capture suture without the hook 524 becoming hung up in the tissue through which it passes to capture suture. The sloped bevel 568 directs the tissue up to the tissue bumper 566 which directs the tissue away from the hook 524. The hook terminus 560 may be observed to have a radius, which is different from previously discussed hook terminus 460, seen in FIG. 10. The ramp relief 570 allows the needle 512 to drop down over the ramps 40a,b, FIG. 5A and provides clearance so that the hook 524 may pick up the suture through the hook entrance 562 and deposit it in the holding area 524.

By eliminating the sliding tubes 318, the needle 512 may be made from larger diameter material, thus stiffening it and improving its ability to transit through tissue with minimal deflection.

To those skilled in the art, the use of a beveled point needle may seem to solve some of the aforementioned problems of spearing the suture by creating a needle that, by virtue of its completely beveled nature, is able to smoothly move over the suture material without snagging. However, it must be noted that a beveled needle, when forced through soft tissue, has a pronounced tendency to wander, and targeting of the needle in order to place it in an advantageous position for the retrieval of the suture material is quite challenging. In fact, this wandering tendency in the direction of the bevel is uncontrollable to the degree that repeatable suture capture is not possible. Another way of ensuring that the needle point does not spear the suture is to have the needle diameter be more than twice the suture diameter, so that the pointed face that interfaces with the suture puts the needle point above the profile of the suture diameter. This, however is a limitation, in that the hole left by the needle as it penetrates the soft tissues is considerably larger than the suture material left in its place.

Although the apparatus described herein are suitable for the placement of mattress stitches, where applicable principles of the invention may be applied to instruments for other stitches, for example, a simple stitch, require only a single needle. Such instruments comprising only a single needle, or, in other instances, perhaps more than two needles, are within the scope of the present invention.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

It is also contemplated that the invention specifically includes combinations of variations of the embodiments described above, or combinations of aspects of variations of the embodiments where applicable.

What is claimed is:

1. A suturing device for deploying a length of suture, the suturing device comprising:
   an elongate tubular housing having a distal portion which is engageable with the length of suture;
   a tissue receiving recess disposed proximally of the distal portion;
   at least a first and a second needle, each having a tissue piercing end and a proximal end, each of the needles being axially movable distally and proximally across the tissue receiving recess; and
   a selecting member located within the housing, the selecting member being rotatable and having an engagement surface disposed within the elongate tubular housing that is rotatable within the housing, wherein the engagement surface is coupled to an actuation member and operable to be axially moveable distally and proximally within the housing upon actuation of the actuation member;
   where the selecting member is rotatable between a plurality of positions including a central position, a first position, and a second position;
   when in the central position, the engagement surface engages a proximal end of at least the first and second needles, when rotated in the first position the engagement surface engages only the first needle, and when in the second position, the engagement surface engages only the second needle, such that when the engagement surface engages the respective needle, axial movement of the engagement surface causes axial movement of the respective needle tissue piercing end.

2. The suturing device of claim 1, where the selecting member further includes a stopping surface rotatable with the selecting member and axially fixed with respect to the housing, where when rotated in the first position, the stopping surface engages the second needle to prevent axial movement; and when rotated in the second position the stopping surface engages the first needle to prevent axial movement.

3. The suturing device of claim 2, where the selecting member comprises a split bushing.

4. The suturing device of claim 3, where the engagement surface is located on a first half of the split bushing.

5. The suturing device of claim 3, where the stopping surface is located on a second half of the split bushing.

6. The suturing device of claim 5, and further comprising a terminus of the hook, the hook terminus being cantilevered proximally from a distal end of the needle.

7. The suturing device of claim 2, further comprising a handle portion coupled to the housing, wherein the handle portion is proximate the actuation member, and wherein the actuation member comprises a needle deployment lever coupled to the engagement surface, where actuation of the needle deployment lever causes axial movement of the engagement surface.

8. The suturing device of claim 7, further comprises a rotatable member on an exterior surface of the device, where the rotatable member is coupled to the selecting member, such that rotation of the rotatable member results in rotation of the selecting member.

9. The suturing device of claim 7, and further comprising a bump on the needle in a location opposed to the hook terminus.

10. The suturing device of claim 2, where the elongate tubular housing includes a passage defining a first cross-sectional area, and where the engagement surface has a cross-sectional area less than that of the first cross-sectional area.

11. The suturing device of claim 1, wherein each needle comprises a distal point, a proximal shaft, and a hook defining a suture holding area.

12. The suturing device of claim 1, wherein the distal portion includes a suture cartridge removably affixed thereto and where the suture cartridge holds the suture.

13. The suturing device of claim 1, further comprising a jaw having a tissue grasping portion and a cam portion having a profile, where the tissue grasping portion and cam portion are located on substantially opposite ends of the jaw;
   at least one jaw engaging surface proximal to the tissue receiving recess;
   where axial movement of the jaw causes the cam portion to engage at least one of jaw engaging surface to further cause a rotational movement of the tissue grasping portion such that the tissue grasping portion moves axially and rotationally with respect to the tissue receiving recess.

14. The suturing device of claim 13, where a portion of the tissue receiving recess includes at least one protrusion to form a second jaw portion.

15. A method of suturing soft tissue with a device as recited in claim 1, the method comprising
   (a) selecting a first needle to deploy;
   (b) grasping a first tissue portion;
   (c) deploying said first needle and drawing a first suture leg through said first tissue portion;
   (d) grasping a second tissue portion;
   (e) selecting the second needle to deploy; and
   (f) deploying said second needle through said second tissue portion and drawing a second suture leg through said second tissue portion.

16. The method of suturing soft tissue as recited in claim 15 further comprising loading a second suture in said device and repeating said steps (a) through (f) to draw a third suture leg and fourth suture leg through a third tissue portion and a fourth tissue portion respectively.

17. The method of claim of claim 15 wherein said first tissue portion and said second tissue portion are across a tear.

* * * * *